US00PP09585P

United States Patent [19]

Glicenstein

[11] Patent Number: Plant 9,585

[45] Date of Patent: Jun. 18, 1996

[54] CHRYSANTHEMUM PLANT NAMED 'FIERY BARBARA'

[75] Inventor: Leon Glicenstein, Salinas, Calif.

[73] Assignee: Yoder Brothers Inc., Barberton, Ohio

[21] Appl. No.: 366,499

[22] Filed: Dec. 30, 1994

[51] Int. Cl.[6] ..... A01H 5/00

[52] U.S. Cl. ..... Plt./82

[58] Field of Search ..... Plt./76, 81, 82

[56] References Cited

U.S. PATENT DOCUMENTS 4,616,099 10/1986 Sparkes ..... 47/58

OTHER PUBLICATIONS

Broertjes, et al., 1980, "A mutant of mutant of a . . . Irradiation of progressive radiation–induced mutants in mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–174.

Searle, et al., 1968, "Chrysanthemums the Year Round", Blanford Press, London, pp. 27–29, 320–327.

Chan, 1966, "Chrysanthemum rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X– and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Fiery Barbara particularly characterized by its flat capitulum form; greyed-red ray floret color; diameter across face of capitulum of 32 to 41 mm when fully opened; branching pattern is spreading and prolific; natural season flower date of Sep. 26 to 30 when planting rooted cuttings on Jun. 15 to 18 in Hightstown, N.J.; plant height of 30 to 38 cm when grown in fall under natural daylength with no growth regulators in New Jersey; excellent, uniform growth habit; and good flexibility of plant for handling, packing and shipping.

1 Drawing Sheet

The present invention comprises a new and distinct cultivar of Chrysanthemum, botanically known as *Dendranthema grandiflora,* and referred to by the cultivar name Fiery Barbara.

Fiery Barbara, identified as 9646 (89-764B04), is a product of a mutation induction program. The new cultivar was discovered and selected by inventor Leon Glicenstein on Apr. 9, 1992 in a controlled environment in Salinas, Calif. as one flowering plant within a flowering block established as rooted cuttings from stock plants which had been exposed as unrooted cuttings to an X-ray source of 1500 rads in Fort Myers, Fla. on Oct. 24, 1991. The irradiated parent cultivar was the cultivar Barbara, disclosed in U.S. Plant Pat. No. 8,607, and described as a decorative garden mum with dark red-purple flower color.

The irradiation program resulting in Fiery Barbara had as its primary objective the expansion of color ranges of the parent cultivar Barbara. The irradiation program comprised irradiation cuttings of the parent cultivar at irradiation levels of 1500, 1750 and 2000 rads. A total of 618 cuttings harvested from a total of 225 irradiated plants were planted on Feb. 24, 10 and 3, 1992, respectively. Of these, 6 initial selections were made, which selections were then revegetated and reflowered. Three consecutive flowerings resulted in discarding 5 of the original 6 selections on Dec. 16, 1992. One code, which showed a mixture of colors, was reselected prior to discarding the original code. The remaining selection and reselection were maintained as PIs (Possible Introductions) and further trialed in Salinas, Calif., Hightstown, N.J. and Leamington, Ontario, Canada, ultimately resulting in the decision to introduce the one selection as Fiery Barbara, and the reselection as Zesty Barbara, disclosed in pending application Ser. No. 08/366,475.

The first act of asexual reproduction of Fiery Barbara was accomplished when vegetative cuttings were taken from the initial selection in Jun. 1992 in a controlled environment in Salinas, Calif., by technicians working under supervision of Leon Glicenstein.

Horticultural examination of controlled flowerings of successive plantings has shown that the unique combination of characteristics as herein disclosed for Fiery Barbara are firmly fixed and are retained through successive generations of asexual reproduction.

Fiery Barbara has not been observed under all possible environmental conditions. The phenotype may vary significantly with variations in environment such as temperature, light intensity and daylength, without, however, any variance in genotype.

The following observations, measurements and comparisons describe plants grown in controlled open areas in Hightown, N.J. Rooted cuttings were established in soil and maintained outdoors under the natural temperature and daylength prevailing during June through October.

The following traits have been repeatedly observed and are determined to be basic characteristics of Fiery Barbara, which, in combination, distinguish this Chrysanthemum as a new and distinct cultivar:

1. Flat capitulum form.
2. Decorative capitulum type.
3. Greyed-red ray floret color.
4. Diameter across face of capitulum of 32 to 41 mm when fully opened.
5. Branching pattern is spreading and prolific.
6. Natural season flower date of Sep. 26 to Sep. 30 when planting rooted cuttings on Jun. 15 to Jun. 18 in Hightstown, N.J.
7. Plant height of 30 to 38 cm when grown in fall under natural daylength with no growth regulators in New Jersey.
8. Excellent, uniform growth habit.
9. Good flexibility of plant for handling, packing and shipping.

The accompanying photographic drawing is a color photograph of Fiery Barbara grown as a pinched garden mum under natural season outside conditions in Salinas, Calif., with the colors being as nearly true as possible with illustrations of this type. Plants were grown outside and dug and transplanted into 15 cm pots at flowering time for photography purposes.

Of the commercial cultivars known to the inventor, the most similar in comparison to Fiery Barbara is the parent cultivar Barbara. All traits of Fiery Barbara are similar to those of Barbara, except for the ray floret color and the number of disc florets. The ray floret color of Fiery Barbara is greyed-red, while the ray floret color of Barbara is dark red-purple. In addition, in most flowering trials, Fiery Barbara has more disc florets in the center of the flower than Barbara.

In the following description, color references are made to The Royal Horticultural Society Colour Chart. The color values were determined on plant material grown as a pinched garden mum grown under natural season outside conditions in Salinas, Calif. on Aug. 21, 1994.

Classification:

*Botanical.*—*Dendranthema grandiflora,* cv., Fiery Barbara.

Commercial.—Flat decorative garden mum.

INFLORESCENCE

Capitulum:

*Form.*—Flat.

*Type.*—Decorative.

*Diameter across face.*—32 to 41 mm when fully opened.

Corolla of ray florets:

*Color (general tonality from a distance of three meters).*—Greyed-red.

*Color (upper surface).*—181A.

*Color (under surface).*—24D, very strongly overlaid with 181A.

*Shape.*—Cross section concave, longitudinal section of outer ray florets straight.

Corolla of disc florets:

*Color (mature).*—9A.

*Color (immature).*—144C.

Reproductive organs:

*Androecium.*—Present on disc florets only; scant pollen.

*Gynoecium.*—Present on both ray and disc florets.

PLANT

General appearance:

*Height.*—30 to 38 cm when grown in fall under natural daylength with no growth regulators in New Jersey.

*Branching pattern.*—Spreading and prolific.

Foliage:

*Color (upper surface).*—147A.

*Color (under surface).*—147B.

*Shape.*—Small, slightly lobed, slightly serrated.

It is claimed:

1. A new and distinct Chrysanthemum plant named Fiery Barbara, as described and illustrated.

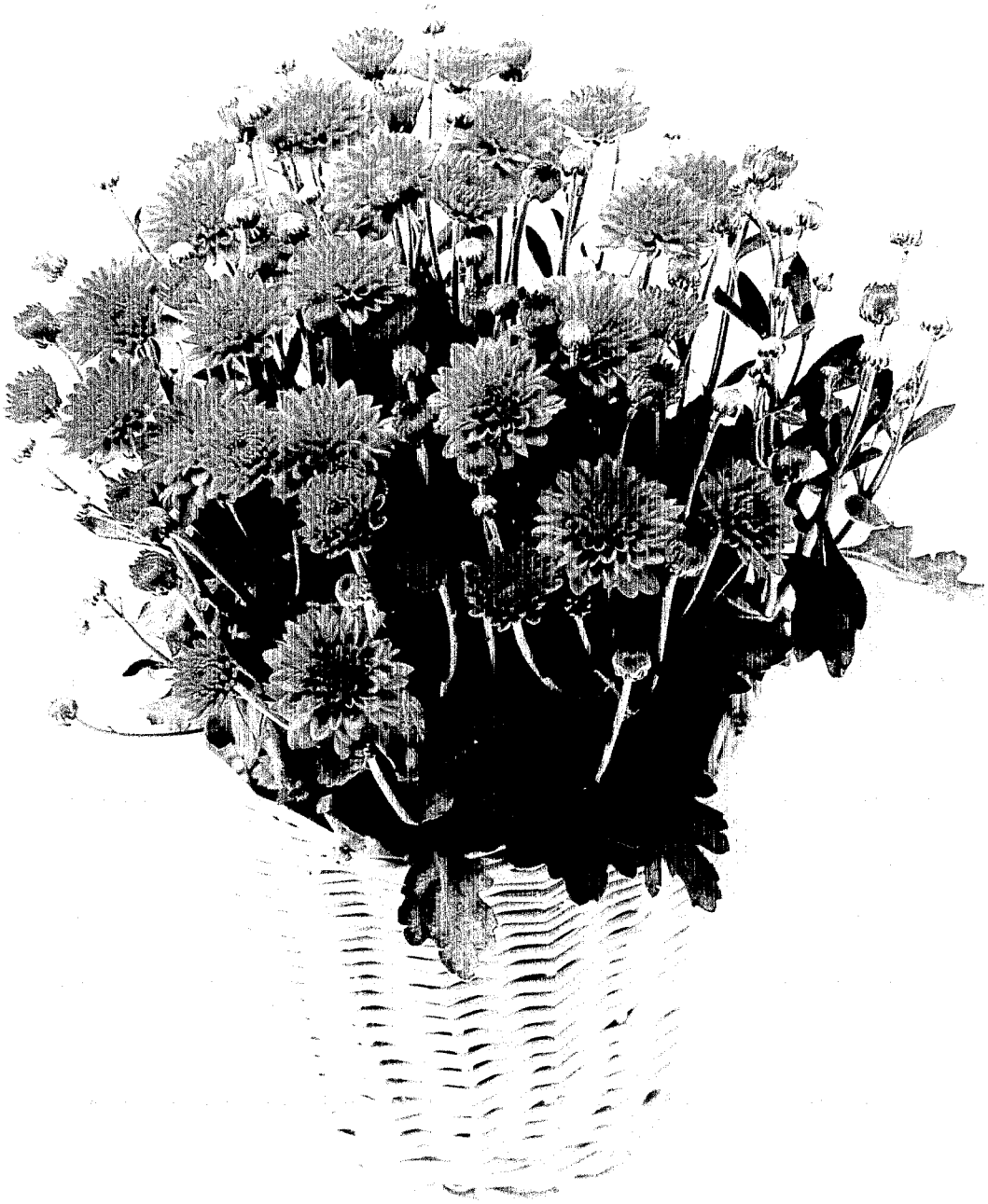

* * * * *